US011879153B1

(12) United States Patent
Tan et al.

(10) Patent No.: US 11,879,153 B1
(45) Date of Patent: Jan. 23, 2024

(54) FLUORESCENT PCR METHOD FOR NUCLEIC ACIDS DETECTION USING THE COMBINATION OF PRIMER-ACTIVATED POLYMERIZATION AND PROBES

(71) Applicant: BIOVUE TECHNOLOGY LTD, Shanghai (CN)

(72) Inventors: Ruoying Tan, Shanghai (CN); Fengwu Zhang, Shanghai (CN); Xinchang Wang, Shanghai (CN); Qing Cong, Shanghai (CN)

(73) Assignee: BIOVUE TECHNOLOGY LTD, Shanghai (CN)

( * ) Notice: Subject to any disclaimer, the term of this patent is extended or adjusted under 35 U.S.C. 154(b) by 0 days.

(21) Appl. No.: 18/045,833

(22) Filed: Oct. 12, 2022

(30) Foreign Application Priority Data

Jul. 13, 2022 (CN) ......................... 202210828832.7
Aug. 31, 2022 (CN) ......................... 202211053951.6

(51) Int. Cl.
*C12Q 1/68* (2018.01)
*C12Q 1/686* (2018.01)
*C12Q 1/6848* (2018.01)
*C12Q 1/6806* (2018.01)

(52) U.S. Cl.
CPC .......... *C12Q 1/686* (2013.01); *C12Q 1/6806* (2013.01); *C12Q 1/6848* (2013.01); *C12Q 2600/16* (2013.01)

(58) Field of Classification Search
CPC .... C12Q 1/686; C12Q 1/6806; C12Q 1/6848; C12Q 2600/16
See application file for complete search history.

(56) References Cited

U.S. PATENT DOCUMENTS 5,677,152 A * 10/1997 Birch ........................ C12N 9/99 435/6.12
7,329,492 B2 * 2/2008 Hardin ................. C12Q 1/6869 435/6.12
7,928,207 B2 * 4/2011 Bodepudi .............. C07H 21/00 435/5
9,434,988 B2 * 9/2016 Behlke ................. C12Q 1/6858
11,268,140 B2 * 3/2022 Ding .................... C12Q 1/6844
2020/0318182 A1 * 10/2020 Gunderson ............. C40B 50/14

OTHER PUBLICATIONS

Milbury, et al. Clinical Chemistry, 2009, 55:4, p. 632-640 (Year: 2009).*
Chen et al. (Frontiers in Microbiology, 2014, 5(305):1-11) (Year: 2014).*

* cited by examiner

*Primary Examiner* — Stephanie K Mummert
(74) *Attorney, Agent, or Firm* — Jun He Law Offices P.C.; Zhaohui Wang

(57) ABSTRACT

The present invention relates to a method for detecting nucleic acids by fluorescent PCR. The method combines primer-activated polymerization reaction and specific fluorescence-labeled probe, which detects the target nucleic acid with high selectivity and high specificity.

11 Claims, 7 Drawing Sheets

Specification includes a Sequence Listing.

SEQUENCE LISTING

```
Sequence total quantity: 8
SEQ ID NO: 1            moltype = DNA  length = 23
FEATURE                 Location/Qualifiers
source                  1..23
                        mol_type = other DNA
                        organism = synthetic construct
SEQUENCE: 1
acctccaccg tgcagctcat cat                                          23

SEQ ID NO: 2            moltype = DNA  length = 23
FEATURE                 Location/Qualifiers
source                  1..23
                        mol_type = other DNA
                        organism = synthetic construct
SEQUENCE: 2
tttgtgttcc cggacatagt cca                                          23

SEQ ID NO: 3            moltype = DNA  length = 23
FEATURE                 Location/Qualifiers
source                  1..23
                        mol_type = other DNA
                        organism = synthetic construct
SEQUENCE: 3
tttgtgttcc cggacatagt cca                                          23

SEQ ID NO: 4            moltype = DNA  length = 18
FEATURE                 Location/Qualifiers
source                  1..18
                        mol_type = other DNA
                        organism = synthetic construct
SEQUENCE: 4
agccgaaggg catgagct                                                18

SEQ ID NO: 5            moltype = DNA  length = 29
FEATURE                 Location/Qualifiers
source                  1..29
                        mol_type = other DNA
                        organism = synthetic construct
SEQUENCE: 5
cagcatgtca agatcacaga ttttgggcg                                    29

SEQ ID NO: 6            moltype = DNA  length = 23
FEATURE                 Location/Qualifiers
source                  1..23
                        mol_type = other DNA
                        organism = synthetic construct
SEQUENCE: 6
cctccttact ttgcctcctt ctg                                          23

SEQ ID NO: 7            moltype = DNA  length = 23
FEATURE                 Location/Qualifiers
source                  1..23
                        mol_type = other DNA
                        organism = synthetic construct
SEQUENCE: 7
cctccttact ttgcctcctt ctg                                          23

SEQ ID NO: 8            moltype = DNA  length = 25
FEATURE                 Location/Qualifiers
source                  1..25
                        mol_type = other DNA
                        organism = synthetic construct
SEQUENCE: 8
ctgggtgcgg aagagaaaga atacc                                        25
```

FLUORESCENT PCR METHOD FOR NUCLEIC ACIDS DETECTION USING THE COMBINATION OF PRIMER-ACTIVATED POLYMERIZATION AND PROBES

CROSS-REFERENCE TO RELATED APPLICATIONS

This application claims priority to Chinse Patent Application No. 202210828832.7, filed on Jul. 13, 2022, and Chinese Patent Application No. 202211053951.6, filed on Aug. 31, 2022, the disclosure of which is incorporated herein by reference.

SEQUENCE LISTING

The sequence listing that is contained in the file named "SEQUENCE LISTING", which is 8,162 bytes and was created on Sep. 14, 2022, is filed herewith by electronic submission and is incorporated by reference herein.

FIELD OF THE INVENTION

The present disclosure relates to the field of molecular biology and particularly methods for polymerase chain reaction amplification and quantitative detection of nucleic acids. Specifically, the present disclosure relates to a quantitative PCR method for detecting nucleic acids using primer-activated polymerization in combination with a fluorescent probe, such as the quantitative PCR method using pyrophosphorolysis-activated polymerization (PAP) in combination with a fluorescent probe.

BACKGROUND OF THE INVENTION

Polymerase chain reaction (PCR), a method for amplifying specific DNA fragments, is widely used in various applications such as diagnosis of genetic diseases, criminal investigation and crime solving, gene cloning and DNA sequence determination. Conventional PCR reactions are somewhat fault tolerant due to the complementarity of primers and template DNA, resulting in non-specific amplification in the presence of large amounts of non-target sequence DNA. Therefore, it is often not possible to use conventional PCR reactions to detect trace or small amounts of mutant sequences in samples where large amounts of wild-type DNA are present.

Primer-activated polymerization reaction is a special type of nucleic acid amplification reaction that allows the precise detection of template DNA in the presence of strong background DNA, providing an important tool for the detection of low-frequency mutations or rare mutations in the clinical or scientific field. The primer-activated polymerization system uses a type of specifically modified blocked primer (e.g., a primer modified at the 3' end with a dideoxynucleotide) that can only be used in a polymerase-mediated DNA strand synthesis reaction when the primer is complementarily bound to the template DNA strand and unblocked (activated) by the action of a deblocking agent. Therefore, primer-activated polymerization reaction requires the primer to precisely complement to the template and be activated before triggering the polymerization reaction. Compared to conventional PCR, this reaction is characterized by the high selectivity of the specifically modified primers and the high specificity of the reaction, which ensures that the amplification product is not generated by the hybridization between the primer and the background DNA sequence, significantly reducing the false positives of the reaction.

Typical primer-activated polymerization reactions include pyrophosphorolysis-activated polymerization (PAP), which uses a modified primer blocked at 3' end with a dideoxynucleotide. In a suitable reaction system, the PAP reaction utilizes the pyrophosphorolysis serially coupled with polymerization by DNA polymerase for nucleic acid amplification (Liu Q, Sommer S S, Biotechniques 2000, 29:1072-1076, 1078,1080). In the absence of a template or when the blocked primer is not complementary to the template, the 3' terminal dideoxynucleotide of the blocked primer cannot be removed through pyrophosphorolysis and the failure to activate the primer precludes subsequent DNA polymerase mediated polymerase. Only when the blocked primer is complementary to the template, the DNA polymerase undergoes pyrophosphorolysis under pyrophosphate buffer conditions to unblock the 3' end of the primer and the DNA polymerase can undergo template dependent polymerization via primer extension. In contrast to conventional PCR, the PAP technique uses a blocked primer modified with a dideoxynucleotide at the 3' end, and utilizes the pyrophosphorolysis and polymerization activity of the DNA polymerase to activate the primer and synthesize DNA. The combination of the pyrophosphorolysis activity and the polymerization reaction results in high selectivity and unparalleled specificity of PAP reaction.

The amplification products of PCR reactions can be detected by fluorescent methods. The fluorescent methods currently used to detect nucleic acid amplification can be divided into two main categories: 1) non-specific fluorescent labeling dye methods (e.g., SYBR Green I), and 2) specific fluorescence-labeled probe methods (e.g., TaqMan® probes). In a non-specific fluorescent labeling dye method, dyes can non-specifically embed in double-stranded DNA to emit strong fluorescence during PCR amplification. However, non-specific amplification or primer dimer formation can also produce false signals, and the dye method cannot be used for multiplex PCR amplification to distinguish among multiple target nucleic acids. The specific fluorescent labeling method with probes uses Taq DNA polymerase to hydrolyze the probe bound to the template DNA by its 5'→3' nucleic acid exonuclease activity during polymerization and extension, releasing the fluorophore and emitting fluorescence, which is highly specific, sensitive and reproducible. At the same time, multiplex PCR can be performed with probes labeled with different fluorophores to distinguish multiple target nucleic acids.

The *E. coli* DNA polymerase I with the F762Y mutation or Taq DNA polymerase with the F667Y mutation (Taq-F667Y) has a ddNTP incorporation activity more than 2000-fold than that of *E. coli* DNA polymerase I or Taq DNA polymerase (Taq), respectively (Tabor S and Richardson C C, Proc. Natl. Acad. Sci., 1995, 92: 6339-6343). The DNA replication fidelity of Taq with the N fragment (280 amino acids at the N terminus) removed (KlenTaq) is 2.8-fold higher than that of full-length Taq (Barnes W M, Gene, 1992, 112: 29-35). KlenTaq has 5'→3' DNA polymerase activity but not 5'→3' DNA exonuclease activity. DNA polymerases currently used in the PAP technique, such as KlenTaq-s (KlenTaq-s is KlenTaq with the F667Y mutation), have pyrophosphatase activity and 5'→3' DNA polymerase activity, but have no 5'→3' exonuclease activity, which does not allow enzymatic cleavage of the probe and cannot be used to detect the amplification products of the PCR reaction using a fluorescent probe. In contrast, the dye method for PAP technology has the drawbacks of poor specificity and inability to distinguish between multiple targets. CN111172245A discloses a fluorescent PCR method to measure nucleic acids by detecting pyrophosphorolysis activated fluorescence. A fluorophore-quencher dual-attached blocked primer was used for PAP which has a fluorophore attached to a nucleotide in the internal region or at the 5' end and a quencher attached to a blocked nucleotide at the 3' end. The fluorophore will fluoresce once the 3' terminal blocker of the primer is removed by pyrophosphorolysis. However, this method can also produce false signals in the event of non-specific amplification or primer dimer formation.

Therefore, there is an urgent demand in the field for the development of a highly selective and specific nucleic acid detection method that can combine a blocked primer-activated polymerization reaction with a specific fluorescence-labeled probe.

SUMMARY OF INVENTION

One aspect of the present disclosure provides a method for detecting nucleic acids combining primer-activated polymerization and specific fluorescence-labeled probe method. In some embodiments, said method comprises:

preparing a PCR reaction system, said PCR reaction system comprising:

(i) a nucleic acid sample comprising or suspected of comprising a target sequence;

(ii) a nucleic acid polymerase or a combination of nucleic acid polymerases, having a 5'→3' polymerase activity and a 5'→3' exonuclease activity;

(iii) a primer pair for amplifying said target sequence to produce an amplicon, said primer pair comprising at least one blocked primer which comprises a blocked nucleotide located at the 3' end of the blocked primer, wherein said blocked nucleotide blocks the extension of said nucleic acid polymerase or combination of nucleic acid polymerases;

(iv) a probe which is complementary to the target sequence or the amplicon, wherein said probe comprises a first nucleotide linked to a fluorophore and a second nucleotide linked to a quencher, wherein the fluorescence signal of said fluorophore is quenched by said quencher when said first nucleotide is not hydrolyzed from said probe, and wherein said nucleic acid polymerase or combination of nucleic acid polymerases is capable of hydrolyzing said first nucleotide from said probe bound to said target sequence or said amplicon during extension such that the fluorescence signal of said fluorophore is not quenched by said quencher; and (v) a deblocking agent which is capable of removing said blocked nucleotide from said blocked primer when said blocked nucleotide anneals to said target sequence or said amplicon, allowing said nucleic acid polymerase or combination of nucleic acid polymerases to extend from said blocked primer;

subjecting said PCR reaction system to amplification reactions under appropriate reaction conditions; and detecting the fluorescence signal of said PCR reaction system.

In some embodiments, said PCR reaction system further comprises:

(vi) a second primer pair for amplifying a second target sequence to generate a second amplicon, said second primer pair comprising a second blocked primer which comprises a second blocked nucleotide located at the 3' end of the second blocked primer, wherein said second blocked nucleotide blocks the extension of said nucleic acid polymerase or combination of nucleic acid polymerases, and (vii) a second probe complementary to the second target sequence or the second amplicon, said second probe comprising a third nucleotide linked to a second fluorophore and a fourth nucleotide linked to a second quencher, wherein the fluorescence signal of said second fluorophore is quenched by said second quencher when said third nucleotide is not hydrolyzed from said probe, and wherein said nucleic acid polymerase or combination of nucleic acid polymerases is capable of hydrolyzing said third nucleotide from said second probe bound to said target sequence or amplicon during extension such that the fluorescence signal of said second fluorophore is not quenched by said second quencher.

In another aspect, the present disclosure provides a method for multiplexed detection of nucleic acids. In some embodiments, said method comprises:

(i) a nucleic acid sample comprising or suspected of comprising a target sequence;

(ii) a nucleic acid polymerase or a combination of nucleic acid polymerases, having a 5'→3' polymerase activity and a 5'→3'exonuclease activity;

(iii) a plurality of primer pairs for separately amplifying said plurality of target sequences to produce a plurality of amplicons, wherein each primer pair comprises a respective blocked primer which comprises a blocked nucleotide located at the 3' end of the blocked primer, wherein said blocked nucleotide blocks the extension of said nucleic acid polymerase or combination of nucleic acid polymerases.

(iv) a plurality of probes which are complementary to said plurality of target sequences or corresponding amplicon, respectively, wherein each probe comprises a first nucleotide attached to a fluorophore and a second nucleotide attached to a quencher, respectively, wherein the fluorescence signal of said fluorophore is quenched by said quencher when said first nucleotide is not hydrolyzed from said probe, and wherein said nucleic acid polymerase or combination of nucleic acid polymerases is capable of hydrolyzing said first nucleotide from said probe bound to the target sequence or amplicon during extension, wherein said plurality of probes comprises the same or different fluorophores.

(v) a deblocking agent which is capable of removing said blocked nucleotide from said respective blocked primer when said blocked nucleotide of said respective blocked primer anneals to its corresponding target sequence or amplicon, allowing said nucleic acid polymerase or combination of nucleic acid polymerases to extend from said blocked primer;

subjecting said PCR reaction system to amplification reactions under appropriate reaction conditions; and detecting the fluorescence signal of said PCR reaction system.

In some embodiments, said blocked nucleotide is 2',3'-dideoxyribonucleotides, ribonucleotide residues, 2',3'-SH nucleotides or 2'-O—PO3 nucleotides.

In some embodiments, said nucleic acid polymerase or combination of nucleic acid polymerases comprises a deblocking agent. In some embodiments, said nucleic acid polymerase or combination of nucleic acid polymerases further has a pyrophosphatase activity. In some embodiments, said nucleic acid polymerase or combination of nucleic acid polymerases is selected from the group consisting of (1) *E. coli* DNA polymerase I with the F762Y mutation, (2) Taq DNA polymerase with the F667Y mutation (Taq-F667Y), and (3) Taq DNA polymerase with N fragment truncated and the F667Y mutation (i.e., Taq C terminal fragment with a F667Y mutation, KlenTaq-s) in combination with a DNA polymerase with 5'→3' nucleic acid exonuclease activity. In some embodiments, said nucleic acid polymerase or combination of nucleic acid polymerases may also be modified, such as chemically or antibody modified, to improve the specificity of the nucleic acid polymerase amplification. In some embodiments, said nucleic acid polymerase or combination of nucleic acid polymerases may also be modified with citraconic anhydride. In some embodiments, said nucleic acid polymerase is Taq-F667Y modified with citraconic anhydride (Taq-F667Y/CA). In some embodiments, said combination of nucleic acid polymerases are KlenTaq-s in combination with Taq modified with citraconic anhydride (Taq/CA).

In some embodiments, said deblocking agent is selected from the group consisting of *E. coli* DNA polymerase I with the F762Y mutation, Taq-F667Y, Taq-F667Y/CA, KlenTaq-s, pyrophosphate, trimeric phosphate, RNase H2 and CS5 DNA polymerase, wherein said CS5 DNA polymerase comprises mutation selected from G46E, L329A, Q601R, D640G, I669F, S671F, E678G or a combination thereof.

In some embodiments, said fluorophore of the probe is selected from the group consisting of: FAM, VIC, JOE, NED, TET, HEX, TAMRA, ROX, TEXASRED, CY3, CY5, CY5.5, and CY7.

In some embodiments, said quencher of the probe is selected from the group consisting of: BHQ1, BHQ2, BHQ3, Dabcyl, MGB, and TAMARA.

In some embodiments, said target sequence comprises a mutant nucleotide, and wherein said blocked nucleotide is complementary to said mutant nucleotide.

In some embodiments, said blocked primer further comprises a mismatched nucleotide which is not complimentary to said target sequence when said blocked primer anneals to said target sequence. In some embodiments, said mismatched nucleotide and said probe are complimentary to each other. In some embodiments, said mismatched nucleotide is 2-18 nucleotides apart from said blocked nucleotide.

In some embodiments, said blocked primer is from 8 to 70 nucleotides in length.

In some embodiments, said method further comprises detecting the amplification Ct (threshold cycle) value of said amplicon.

In some embodiments, said nucleic acid sample comprises modified or unmodified single-stranded DNA, double-stranded DNA, RNA, cRNA or a combination thereof.

It should be understood that, within the scope of the present disclosure, each of the technical features described above and each of the technical features specifically described below (e.g., in Examples) may be combined with each other so as to constitute new or preferable technical solutions. For reasons of space, no exhaustive description will be given herein.

DETAILED DESCRIPTION OF THE INVENTION

Figure 1:
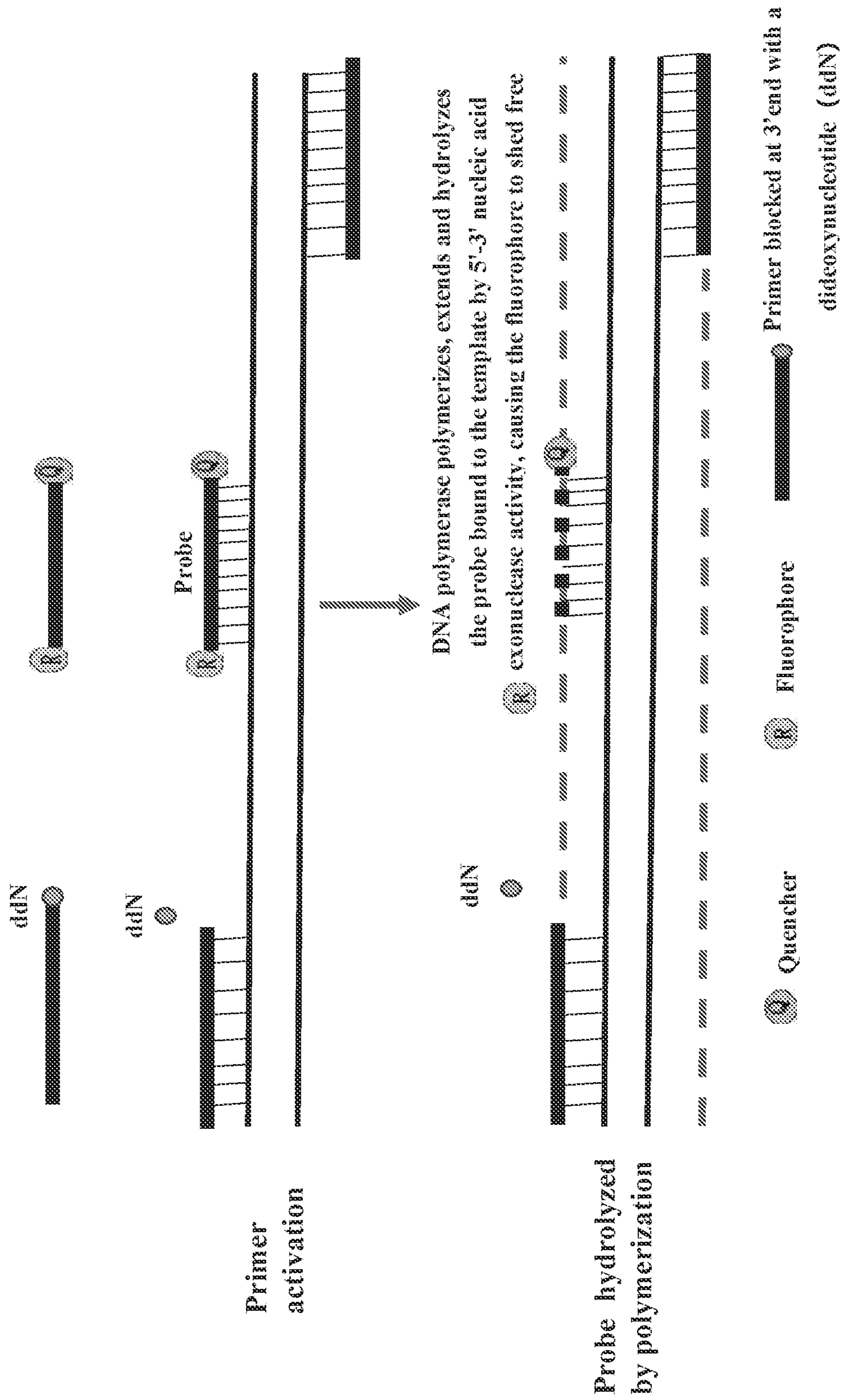
FIG. 1 illustrates the principle of detection of nucleic acids by a primer-activated polymerization combined with probes.

One aspect of the present disclosure provides a novel fluorescent PCR method for detection of nucleic acids by primer-activated polymerization combined with probes, including singleplex fluorescent PCR and multiplex fluorescent PCR. The singleplex fluorescent PCR combined with a primer-activated polymerization comprises a combination of a probe and a primer pair which has at least one blocked primer, allowing for highly selective and specific detection of the corresponding target sequence. Multiplex fluorescent PCR combined with primer-activated polymerization comprises the combination of N primer pairs (N>1) and N probes, each primer pair containing at least one blocked primer. Multiple fluorophore-quencher dual-labeled probes can be used to conduct multiplex fluorescent PCR which utilizes different fluorophores and amplification Ct values to detect multiple target sequences.

The following description of the present disclosure is intended to illustrate only various embodiments of the present disclosure. Accordingly, the specific modifications discussed should not be construed as limiting the scope of the present disclosure. It will be apparent to those skilled in the art that various equivalents, modifications and amendments can be obtained without departing from the scope of the present disclosure, and it should be understood that said equivalent embodiments will be included herein. All references cited herein, including publications, patents, and patent applications, are incorporated herein by reference in their entirety.

Definitions

As used herein, "a", "an" and "the" refer to one (species) or more than one (species) (i.e., at least one (species)) grammatical object of said article. For example, "a protein" means one protein or more than one protein.

The term "about" refers to a value or composition within an acceptable margin of error for a particular value or composition as determined by a person of ordinary skill in the art, which will depend in part on how the value or composition is measured or determined.

As used herein, the term "polymerase chain reaction" or "PCR reaction" refers to a nucleic acid amplification reaction that amplifies a nucleic acid containing a specific sequence. Conventional PCR reaction systems include template DNA, nucleic acid polymerase, primers, dNTP, $Mg^{2+}$, and buffer. The conventional PCR reaction consists of a series of cyclic warming steps, each cycle starting with denaturing the template DNA to single-stranded at high temperature (often around 95° C.), then allowing the primer to anneal to the single-stranded template DNA by base complementary pairing at low temperature (often around 60° C.), and then tempering to the optimal reaction temperature for DNA polymerase (around 72° C.), allowing DNA polymerase to synthesize the complementary strand in the direction of phosphate to pentose (5'-3'), thus allowing the amount of template DNA to be multiplied in each cycle.

As used herein, the term "fluorescent PCR reaction" refers to a method that combines a PCR reaction with a fluorescence detection technique, allowing quantitative monitoring of nucleic acid amplification based on the intensity of the monitored fluorescence signal.

As used herein, the terms "fluorophore" and "fluorescent molecule" are used interchangeably and refer to a group or molecule that produces fluorescence. When a fluorophore absorbs light energy at short wavelengths, it can emit fluorescence at longer wavelengths. Each fluorophore has a characteristic absorption spectrum and a characteristic emission spectrum. The particular wavelength at which the fluorophore most efficiently absorbs energy is called peak absorption, while the wavelength at which the fluorophore most efficiently emits fluorescence is called peak emission. In some embodiments, said fluorophore is selected from the group consisting of FAM, VIC, JOE, NED, TET, HEX, TAMRA, ROX, TEXASRED, CY3, CY5, CY5.5, and CY7.

As used herein, the terms "quencher", "quenching molecule" or "quenching agent" are used interchangeably and refer to a group or molecule that reduces the fluorescence intensity of the output of a fluorophore. They have characteristic absorption spectra and absorption peaks. For the mechanism of fluorescence resonance energy transfer (FRET) to work, the absorption spectrum of the quenching group should overlap with the emission spectrum of the fluorophore and be sufficiently close to the fluorescent group, e.g., not more than 30 nucleotides. In some embodiments, said quencher is selected from the group consisting of: BHQ1, BHQ2, BHQ3, Dabcyl, MGB and TAMARA.

As used herein, the term "pyrophosphorolysis reaction" or "pyrophosphorolysis" is the reverse reaction of the deoxyribonucleic acid polymerization. In specific embodiments, in the presence of pyrophosphate, the polymerase removes the 3' terminal nucleotide from the double-stranded DNA to produce a nucleoside triphosphate and a double-stranded DNA with said 3' terminal nucleotide removed: $[dNMP]_n + PPi \rightarrow [dNMP]_{n-1} + dNTP$ (Deutscher and Kornberg, 1969).

As used herein, the term "primer", refers to a macromolecule with a specific nucleotide sequence that is used to stimulate synthesis. A primer is used in the initiation of a nucleic acid amplification reaction (or nucleotide polymerization) and hydrogen-bonded to the reactant. In specific embodiments, primers appear in pairs (i.e., primer pairs), which are usually two synthetic oligonucleotide sequences. One primer is complementary to a DNA template strand at one end of the region to be amplified and the other primer is complementary to another DNA template strand at the other end of the region to be amplified, and both primers function as a starting point for nucleotide polymerization from which the nucleic acid polymerase can start the synthesis of a new nucleic acid strand at its 3' end. In some embodiments, the length of each primer in said primer pair is each independently from 8 to 70 nucleotides; preferably, from 8 to 50 nucleotides; optimally, from 8 to 30 nucleotides.

As used herein, the terms "nucleic acid" and "polynucleotide" are used interchangeably and refer to a polymeric form of any length of nucleotide (e.g., deoxyribonucleotide or ribonucleotide) or an analog thereof. Polynucleotides can have any three-dimensional structure and can have any known or unknown function. Non-limiting examples of polynucleotides include genes, gene fragments, exons, introns, messenger RNA (mRNA), transfer RNA, ribosomal RNA, nucleases, cDNA, shRNA, single-stranded short or long RNA, recombinant polynucleotides, branching polynucleotides, plasmids, vectors, isolated DNA of any sequence, regulatory regions, isolated RNA of any sequence, nucleic acid probes and primers. Nucleic acid molecules can be linear or cyclic.

As used herein, the terms "nucleic acid comprising a target sequence", "nucleic acid to be tested" or "target nucleic acid" are used interchangeably and refer to a nucleic acid fragment that is specifically amplified in a fluorescent PCR method, or a nucleic acid fragment that can trigger a detectable signal in a PCR reaction system, or a nucleic acid fragment that can be specifically detected using a nucleic acid detection method. The nucleic acid to be tested in the present disclosure may be a nucleic acid fragment with a site-specific mutation or a trace amount of a specific nucleic acid fragment in a complex context. In some embodiments, said nucleic acid to be tested is not a single nucleic acid fragment to be tested, which may comprise N different nucleic acids to be tested. In some embodiments, the nucleic acids to be tested of the present disclosure comprise modified or unmodified single-stranded DNA, double-stranded DNA, RNA, cDNA, or combinations thereof. In some embodiments, said target nucleic acid comprises a wild type or a mutant.

As used herein, the term "nucleotide" is the basic building block of a nucleic acid. A nucleotide consists of a nitrogenous base as its core, plus a pentose and one or more phosphate groups. There are five nitrogenous bases, adenine (A), guanine (G), cytosine (C), thymine (T) and uracil (U). Nucleotides in which the pentose is deoxyribose are called deoxyribonucleotides (monomers of DNA) while nucleotides in which the pentose is ribose are called ribonucleotides (monomers of RNA). For the purposes of this disclosure, nucleotides include, but are not limited to, deoxyribonucleotide thymine (dTMP), deoxyribonucleoside adenine (dAMP), deoxyribonucleotide guanine (dGMP), deoxyribonucleotide cytosine (dCMP), deoxyribonucleotide uracil (dUMP), etc., or modified versions of the above nucleotides.

As used herein, the term "nucleic acid polymerase" is the one used in primer-activated polymerization systems for the polymerization or extension of deoxyribonucleic acids. Nucleic acid polymerases used in the present disclosure include *E. coli* DNA polymerase I, Taq DNA polymerase, and mutants thereof. In certain embodiments, nucleic acid polymerases used in the present disclosure also have 5'-3' exonuclease activity. In certain embodiments, nucleic acid polymerases used in the present disclosure include *E. coli* DNA polymerase I with the F762Y mutation, Taq DNA polymerase with the F667Y mutation (Taq-F667Y), and Taq DNA polymerase with N fragment excised and with F667Y mutation (KlenTaq-s).

Method for Detecting Nucleic Acids

One aspect of the present disclosure provides a PCR method using primer-activated polymerization combined with a fluorescent probe. Primer-activated polymerization reactions, such as classical PAP reactions, generally use DNA polymerases without 5'-3' exonuclease activity, such as KlenTaq-s, for the primer-activated polymerization reaction. However, commonly used specific fluorescence-labeled probes, such as the Taqman® probe reaction, require hydrolysis of the probe by a DNA polymerase with 5'-3' exonuclease activity to generate a fluorescence signal. As a result, classical PAP reactions generally cannot be combined with fluorescent probes. The method provided by the present disclosure addresses the important drawback that classical PAP reactions are unable to combine a fluorescent probe by combining a blocked primer-activated polymerization reaction with a specific fluorescence label-probe (e.g., Taqman® probe), ensuring the specificity of the amplification while maintaining the amplification efficiency of fluorescent PCR.

Primer-activated polymerization reactions are polymerase chain reactions that contain specifically modified blocked primers in the system. Nucleic acid polymerases are unable to mediate DNA strand synthesis when the blocked primers are not unblocked (i.e., not activated). Therefore, the blocked primer first needs to be unblocked to trigger the polymerization reaction before polymerase can mediate the DNA strand synthesis. The primer-activated polymerization reaction ensures that the unblocking reaction only occurs in the presence of the template DNA sequence in the system, greatly reducing the number of false positives in the reaction.

In some embodiments, primer-activated polymerization is pyrophosphorolysis activated polymerization (PAP) which uses a primer blocked at 3' end (e.g., a dideoxynucleotide) and utilizes pyrophosphorolysis of DNA polymerase coupled with polymerization for nucleic acid amplification (Liu Q, Sommer S S, Biotechniques 2000, 29:1072-1076, 1078,1080). The 3' end of the blocked primer cannot undergo pyrophosphorolysis in the absence of a template or when it is not complementary to the template, resulting in the inability of DNA polymerase to extend. Only when the 3' end of the blocked primer is complementary to the template, DNA polymerase undergoes pyrophosphorolysis under pyrophosphate buffer conditions, removing the blocked 3' end of the primer, and DNA polymerase can extend along the primer and polymerization can occur. Therefore, in some embodiments, the present disclosure provides a method for nucleic acid detection by PAP in combination with a specific fluorescence-labeled probe.

A blocked primer is a primer whose 3' end is blocked to impede extension of the nucleic acid polymerase. In some embodiments, the 3' end of the blocked primer is blocked by a blocked nucleotide. A blocked nucleotide is any nucleotide having a specific structure capable of stopping the extension of nucleic acid polymerase. Examples of blocked nucleotides include, but are not limited to, dideoxyribonucleotides (e.g., 2',3'-dideoxyribonucleotides), ribonucleotides, 2',3' SH nucleotides and 2'-O—$PO_3$ nucleotides.

The blocked primer can be unblocked (i.e., activated) by a deblocking agent under specific conditions (e.g., complementarity of the 3' end blocked nucleotide to the template DNA). The deblocking agent may be any component capable of removing said blocked nucleotide from the blocked primer upon hybridization of the blocked nucleotide to the target sequence. Depending on the blocked nucleotide, deblocking agents include, but are not limited to, modified DNA polymerases *E. coli* DNA polymerase I with the F762Y mutation, Taq-F667Y, Taq-F667Y/CA, KlenTaq-s, pyrophosphate, trimeric phosphate, RNase H2 and CS5 DNA polymerase with specific mutations (said mutations include G46E, L329A, Q601R, D640G, I669F, S671F, E678G or a combination of these mutations), and combinations thereof. In some embodiments, the primer activation step in the present disclosure is achieved by a pyrophosphate activation reaction. In such embodiments, the deblocking agent comprises (1) Taq-F667Y, Taq-F667Y/CA, KlenTaq-s, or other modified DNA polymerase and (2) pyrophosphate.

In some embodiments, the nucleic acid detection method provided by the present disclosure uses probes having a fluorophore-quencher dual-labeling that can detect target sequences in the system by fluorescence signals.

The nucleic acid detection method provided by the present disclosure can be understood by the illustrative embodiment shown in FIG. 1.

FIG. 1 shows an embodiment of detecting nucleic acids by primer-activated polymerization in combination with probes. The detection system comprises or may comprise a nucleic acid sample to be tested, a nucleic acid polymerase, a primer set for amplifying the target sequence to produce an amplicon, a fluorescent probe, and a deblocking agent. The primer set comprises at least one primer pair that has a blocked primer. The fluorescent probe is connected to the fluorophore (R) and the quencher (Q). In the natural state, the fluorescence energy emitted by the fluorophore (R) of the probe is absorbed by the quencher (Q) and no fluorescence signal is detected in the system. When the blocked primer anneals to the target sequence DNA, the blocked primer is activated by removing the 3' terminal dideoxynucleotide in the presence of a deblocking agent. During polymerization and extension, the DNA polymerase hydrolyzes the probe bound to the target DNA or amplicon by 5'-3' nucleic acid exonuclease activity, and the fluorophore (R) of the probe is shed and the fluorescence energy emitted by the fluorophore (R) cannot be absorbed by the quencher (Q). The fluorescence energy emitted by the R group cannot be absorbed by the quencher (Q), thus allowing a fluorescence signal to be detected in the system. When the blocked primer does not match the target sequence or there is no target sequence, the deblocking agent is unable to remove the blocked nucleotide from the block primer and the nucleic acid polymerase is unable to extend from the blocked primer for amplification. It can be understood that, while the fluorophore (R) and the quencher (Q) as illustrated in FIG. 1 are connected at 5'-end and 3'-end of the fluorescent probe respectively, in some embodiments of the present disclosure, the fluorophore (R) and the quencher (Q) can connect at 3'-end and 5'-end of the fluorescent probe respectively. In such embodiments, during the polymerization and extension, the quencher (Q) of the probe is shed and the fluorescence energy is emitted by the fluorophore (R). It can also be understood that in other embodiments of the present disclosure, the fluorophore (R) and the quencher (Q) can connect to the nucleotides in the middle of the fluorescent probe.

In some embodiments, the probe sequence is complementary to the target sequence (or the sequence complementary to the target sequence), as shown in FIG. 1. In some embodiments, the sequence of the primer or blocked primer is partially non-complementary to the target sequence, and the probe sequence can be designed to be complementary to the portion of the primer or blocked primer that is not complementary to the target sequence. In such cases, the probe sequence can be complementary to the sequence of the amplicon and the same assays provided by the present disclosure can be performed.

In some embodiments, the length of the blocked primer is 8 to 70 nucleotides. In some embodiments, the length of the blocked primer is 10, 15, 20, 25, 30, 35, 40, 45, 50, 55, 60, 65 or 70 nucleotides.

In some embodiments, the blocked primer is further modified to reduce the amplification of undesired nucleic acids. Preferably, said modification is the introduction of at least one mismatched nucleotide into the primer that is not complementary to the target sequence when the blocked primer hybridizes to the target sequence. In some embodiments, said mismatched nucleotide is located on the 5' side of the blocked nucleotide. Preferably, wherein said mismatched nucleotide is located 2-18 nucleotides apart from the blocked nucleotide.

As aforementioned, the methods of the present disclosure can detect template nucleic acids comprising target sequences by fluorescence signals. It will be understood that in some embodiments, the fluorescence signal detected in the reaction system may be the reaction background or "noise". As is well known in the art, the amplification signal can be distinguished from the background by a baseline, i.e., the level of fluorescence signal at the initial cycle, and a threshold, i.e., the level of fluorescence signal that is significantly higher than the baseline signal.

In some embodiments, the methods of the present disclosure further comprise the step of detecting an amplification Ct value of the amplicon. Ct (threshold cycle) is the number of cycles in which the fluorescence signal exceeds a threshold value. In some embodiments, the target nucleic acid can be quantified by fluorescent PCR specifically amplifying the fluorescent amplification signal of the target nucleic acid or by detecting the Ct value. Thus, the detection method of the present disclosure can be qualitative or quantitative.

Multiplex Fluorescent PCR Assay

In some embodiments, the methods provided by the present disclosure can simultaneously detect multiple target sequences in a sample. Thus, in another aspect, the present disclosure provides a method for multiplexed nucleic acid detection.

In some embodiments, different target sequences can be distinguished by different fluorescence signals. In some embodiments, the primer pools in the reaction systems of the present disclosure contain different primer sets with multiple probes having different fluorophore-quencher combinations. In this regard, probes with different fluorophores can be designed for different target sequences in the same reaction system (or detection system) to differentiate amplification products of multiple target sequences in a single reaction, while quencher can be selected as the same universal quencher or different quenchers depending on the fluorophore. In some embodiments, the use of N different fluorescence signals may distinguish between N+1 amplification products in a single reaction. In some embodiments, 2, 3, 4, or 5 amplification products can be distinguished in a single reaction.

The present disclosure provides a novel method for detecting nucleic acids by fluorescent PCR that ensures the specificity of fluorescent PCR amplification while maintaining fluorescent PCR amplification efficiency by combining primer-activated polymerization and specific fluorescence-labeled probes.

The fluorescent PCR method of the present disclosure can either perform a singleplex reaction or use multiple fluorophore-quencher dual-labeled probes with different fluorophore in order to differentiate multiple templates in a single reaction to achieve a single-tube multiplex fluorescent PCR reaction, to overcome the difficulties of the fluorescent dye method that SYBR fluorescent PCR cannot perform multiplex reaction and has poor specificity, to simplify the operation, to reduce reagent consumption and to enhance detection sensitivity.

The present disclosure integrates PAP technology with the combined technology of probes and fluorescence PCR, which inherits the characteristics of high sensitivity, high selectivity and high specificity of PAP technology, but also has the function of detecting quantitative and qualitative nucleic acids. The multiplex fluorescence PCR reaction that combines PAP with probes in one tube does not produce cross reactions, solving the problem of non-specific reactions that are prone to occur in multiplex PCR reaction and avoiding the generation of false positive results.

The method of the present disclosure is simple and convenient to operate, and results can be observed in real time. Since neither tube opening nor PCR post-processing is required, PCR products will not be contaminated.

The present invention is further described below together with specific embodiments. It should be understood that these embodiments are intended to illustrate the invention only and are not intended to limit the scope of the invention. Experimental methods for which specific conditions are not indicated in the following embodiments generally follow conventional conditions, such as those described in Sambrook et al, Molecular Cloning: A Laboratory Manual (New York: Cold Spring Harbor Laboratory Press, 1989), or as recommended by the manufacturer. Percentages and parts are percentages by weight and parts by weight unless otherwise stated.

EXAMPLES

Example 1. Materials and Methods

Example 1.1 Preparation of Primers

Two mutant nucleic acid sequences of the human epidermal growth factor receptor (EFGR) gene: T790M (2369C>T) and L858R (2573T>G), which were obtained from the COSMIC database, were used to design specific primers and probes to amplify the mutant sequences using Primer Primier 3.0 software.

Example 1.2 Preparation of Templates

Two mutant nucleic acid sequences of the human epidermal growth factor receptor (EGFR) gene: T790M (2369C>T) and L858R (2573T>G) were obtained from the COSMIC database. The mutant nucleic acid sequences of T790M (2369C>T) and L858R (2573T>G) and their corresponding wild-type gene fragments were chemically synthesized and inserted into the pUC57 vector to construct mutant and wild-type recombinant plasmid DNA, respectively. After transformation of the recombinant plasmid DNA into *E. coli* for propagation, the extracted recombinant plasmid DNA was quantified by UV absorption at 260 nm. Each plasmid was diluted separately with TE buffer to a concentration of 10,000 copies/μl.

Example 1.3 Fluorescent PCR Method for Detecting Nucleic Acids Using Primer-Activated Polymerization Combined with Probes Each reaction mixture contains 50 mM Tris pH 8.0, 0.2 mM dNTP, 3 mM MgCl2, 90 nM pyrophosphate, 2 units of Taq-F667Y or 2 units of Taq-F667Y/CA or a combination of DNA polymerases (2 units of KlenTaq-s and 1 unit of Taq/CA mix), 0.2 μM probes, wild type genomic DNA and/or plasmid DNA, with each blocked primer of 0.5 μM concentration. Add DNAase/RNAase-free water to each reaction mixture to a final volume of 20 μL. Amplification was performed using a SLAN 96S PCR System (Hongshi Medical Technology Co., Ltd, China), running the following program: 95° C. for 10 min; 95° C. for 15 sec, 65° C. for 120 sec, 40 cycles, 65° C. to collect FAM or/and ROX fluorescence signals.

Example 2. Singleplex Detection of EFGR Mutations by Fluorescent PCR Method Based on the Combination of Primer-Activated Polymerization and Probes

Example 2.1 Mutation Detection with Taq-F667Y

A singleplex fluorescent PCR reaction was performed to detect the T790M (2369C>T) mutation using a primer set of an upstream blocked primer (SEQ ID NO: 1) and a downstream blocked primer (SEQ ID NO: 2) and a probe (SEQ ID NO: 4) (Table 1). Another singleplex fluorescent PCR reaction to detect the T790M (2369C>T) mutation used a primer set of an upstream blocked primer (SEQ ID NO: 1) and a downstream unblocked primer (SEQ ID NO: 3) and a probe (SEQ ID NO: 4) (Table 1).

Another singleplex fluorescent PCR reaction to detect the L858R(2573T>G) mutation used a primer set of an upstream blocked primer (SEQ ID NO: 5) and a downstream blocked primer (SEQ ID NO: 6) and a probe (SEQ ID NO: 8) (Table 1). Another singleplex fluorescent PCR reaction was performed to detect the L858R (2573T>G) mutation using a primer set of an upstream blocked primer (SEQ ID NO: 5) and a downstream unblocked primer (SEQ ID NO: 7) and a probe (SEQ ID NO: 8) (Table 1).

Figure 2A:
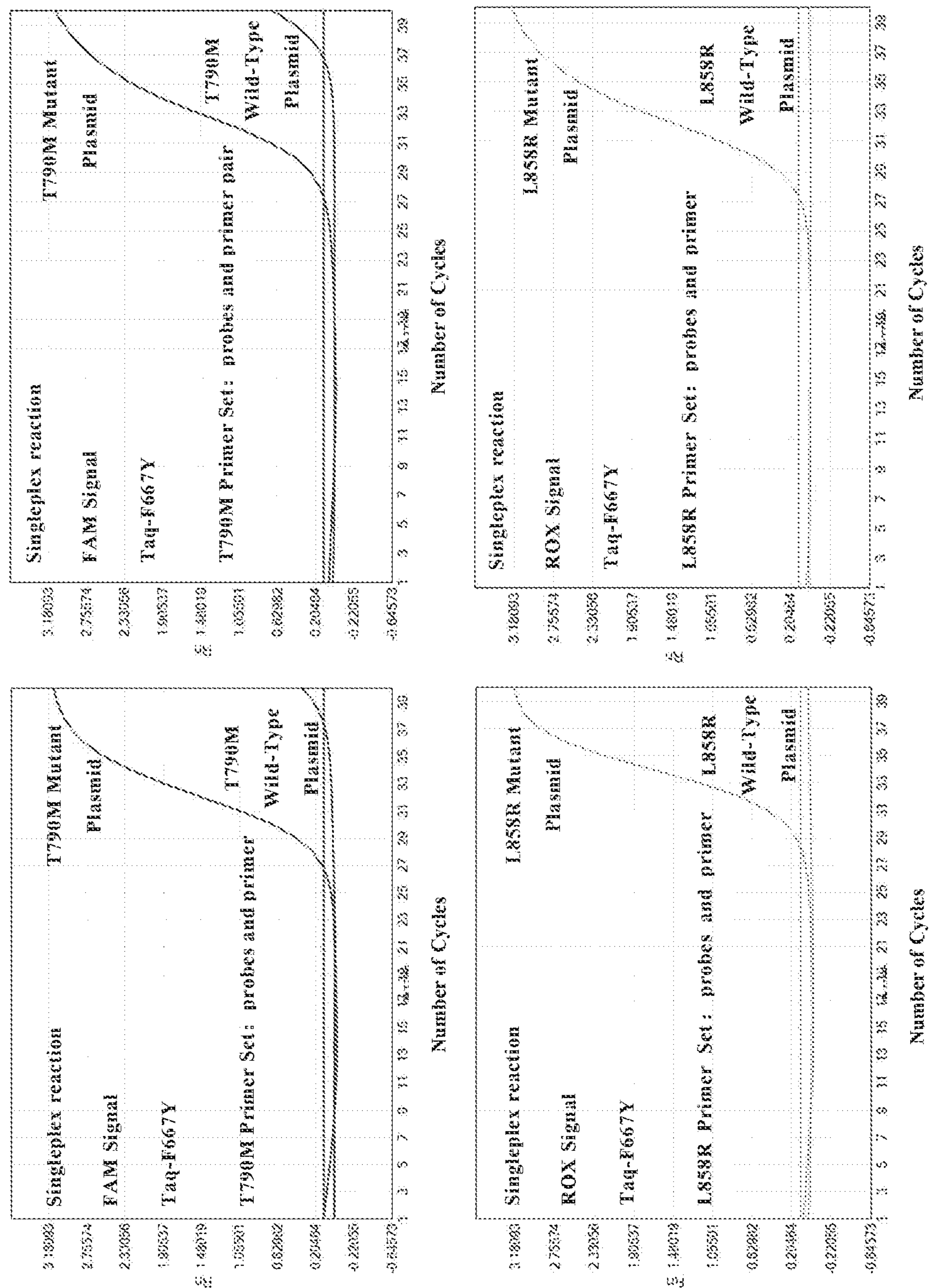
FIG. 2A shows the results of Taq-F667Y for singleplex amplification of mutant and wild-type plasmids by fluorescent PCR with a primer-activated polymerization combined with probes.

The fluorescent PCR reaction system used Taq-F667Y which is an enzyme having pyrophosphatase activity, 5'→3' DNA polymerase activity, and 5'→3' nucleic acid exonuclease activity. When 20,000 copies of the T790M or L858R mutant plasmid were used as templates to amplify the corresponding mutant gene fragments with different primer sets of T790M and L858R, respectively, a fluorescent amplification signal was generated; when 20,000 copies of the wild-type plasmid of T790M or L858R were used as templates for amplification, it was found that the T790M primer sets (probes and primer pair of two blocked primers or probes and primer pair of one blocked primer) showed a weaker non-specific amplification signal, with the primer set of probe and primer pair of one blocked primer performing worse. On the other hand, the L858R primer sets (probes and primer pair of two blocked primers or probes and primer pair of one blocked primer) showed no fluorescent amplification signal (Table 2, FIG. 2A). Based on the combination of primer-activated polymerization and probes, the fluorescent PCR method used Taq-F667Y to perform singleplex detection with the primer set of probe and primer pair of at least one blocked primer. Mutation detection of T790M (2369C>T) produces non-specific amplification under condition of wild-type templates, while the primer set of probes and primer pair of two blocked primers shows better specificity than the primer set of probes and primer pair of one blocked primer.

Example 2.2 Mutation Detection with Taq-F667Y/CA

The primer sets used in Example 2.2 are the same as those used in Example 2.1.

Figure 2B:
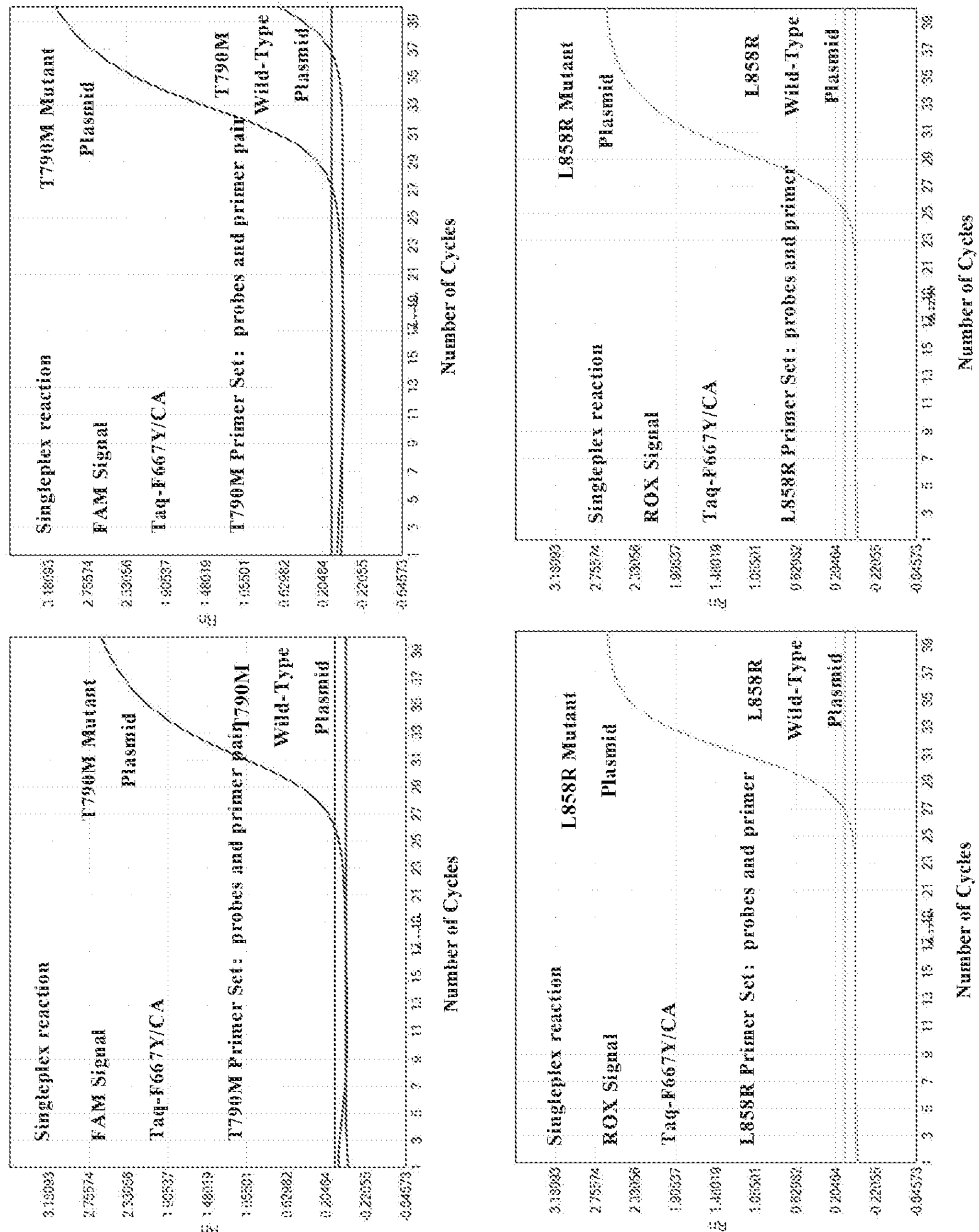
FIG. 2B shows the results of Taq-F667Y/CA for singleplex amplification of mutant and wild-type plasmids by fluorescent PCR with a primer-activated polymerization combined with probes.

The fluorescent PCR reaction system uses Taq-F667Y/CA, which is an enzyme modified with citraconic anhydride (Sigma Aldrich 125318-25g) to inhibit the enzyme activity and activate it by high temperature, and also has pyrophosphatase activity, 5'→3' DNA polymerase activity and 5'→3' nucleic acid exonuclease activity. When 20,000 copies of the T790M or L858R mutant plasmids were used as templates to amplify the corresponding mutant gene fragments with aforementioned different primer sets of T790M and L858R, respectively, a fluorescent amplification signal was generated; when 20,000 copies of the wild-type plasmids of T790M or L858R were used as templates for amplification, it was found that both of the T790M primer set and the L858R primer set had no fluorescent amplification signal (Table 2, FIG. 2B). Based on the combination of primer-activated polymerization and probes, the fluorescent PCR method used Taq-F667Y/CA to perform singleplex detection with the primer set of probe and primer pair of at least one blocked primer. It was found that the fluorescent PCR method have high amplification specificity when using Taq-F667Y/CA, indicating that Taq-F667Y modified with citric anhydride into Taq-F667Y/CA can significantly increase the specificity of the amplification with Taq-F667Y.

Example 2.3 Mutation Detection with the Combination of KlenTaq-s and Taq/CA The primer sets used in Example 2.3 are the same as those used in Example 2.1.

Figure 2C:
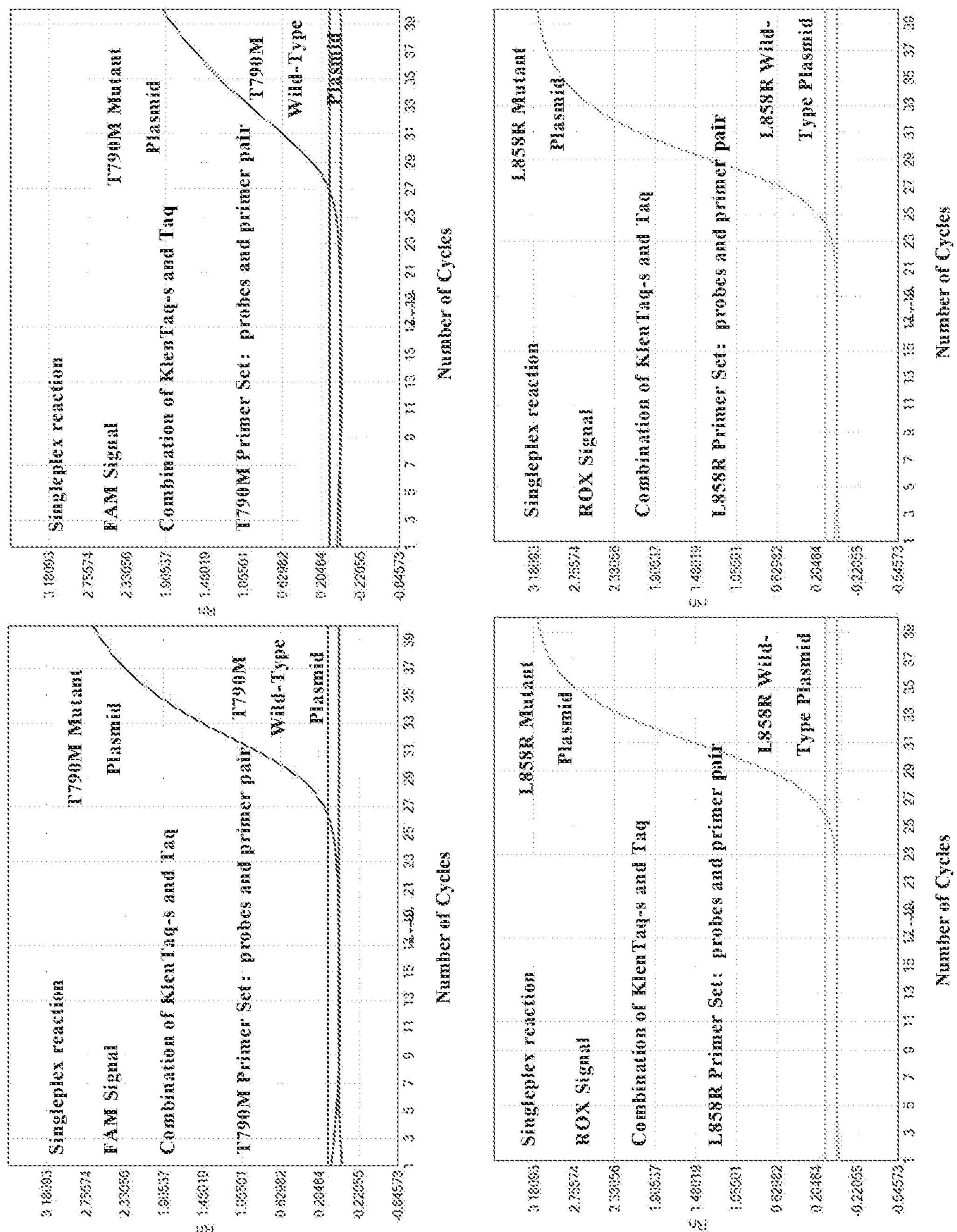
FIG. 2C shows the results of KlenTaq-s in combination with Taq/CA for singleplex amplification of mutant and wild-type plasmids by fluorescent PCR with a primer-activated polymerization combined with probes.

The fluorescent PCR reaction system used a combination of KlenTaq-s and Taq, utilizing the pyrophosphatase activity and the 5'→3' DNA polymerase activity of KlenTaq-s, combined with the 5'→3' DNA polymerase activity and 5'→3' nucleic acid exonuclease activity of Taq enzyme activity. When 20,000 copies of the T790M or L858R mutant plasmids were used as templates to amplify the corresponding mutant gene fragments with aforementioned different primer sets of T790M and L858R, respectively, a fluorescent amplification signal was generated; when 20,000 copies of the wild-type plasmids of T790M or L858R were used as templates for amplification, both had no fluorescent amplification signal (Table 2, FIG. 2C). Based on the combination of primer-activated polymerization and probes, the fluorescent PCR method used the combination of KlenTaq-s and Taq to perform singleplex detection with the primer set of probes and primer pair of at least one blocked primer. It was found that the fluorescent PCR method have good specificity, indicating that Taq-F667Y/CA and the combination of KlenTaq-s and Taq/CA were comparable in amplification specificity.

Example 3. Multiplex Detection of EGFR Gene Mutation by Fluorescent PCR Method Based on the Combination of Primer-Activated Polymerization and Probes

Example 3.1 Mutation Detection with Taq-F667Y

A duplex fluorescent PCR reaction was performed to detect T790M and L858R mutations simultaneously using a primer pool composed of T790M primer set (an upstream blocked primer (SEQ ID NO: 1) and a downstream blocked primer (SEQ ID NO: 2) and a probe (SEQ ID NO: 4)) and L858R primer set (an upstream blocked primer (SEQ ID NO: 5) and a downstream blocked primer (SEQ ID NO: 6) and a probe (SEQ ID NO: 8)).

Another duplex fluorescent PCR reaction was performed to detect T790M and L858R mutations simultaneously using a primer pool composed of T790M primer set (an upstream blocked primer (SEQ ID NO: 1) and a downstream blocked primer (SEQ ID NO: 3) and a probe (SEQ ID NO: 4)) and L858R primer set (an upstream blocked primer (SEQ ID NO: 5) and a downstream blocked primer (SEQ ID NO: 7) and a probe (SEQ ID NO: 8)).

Figure 3A:
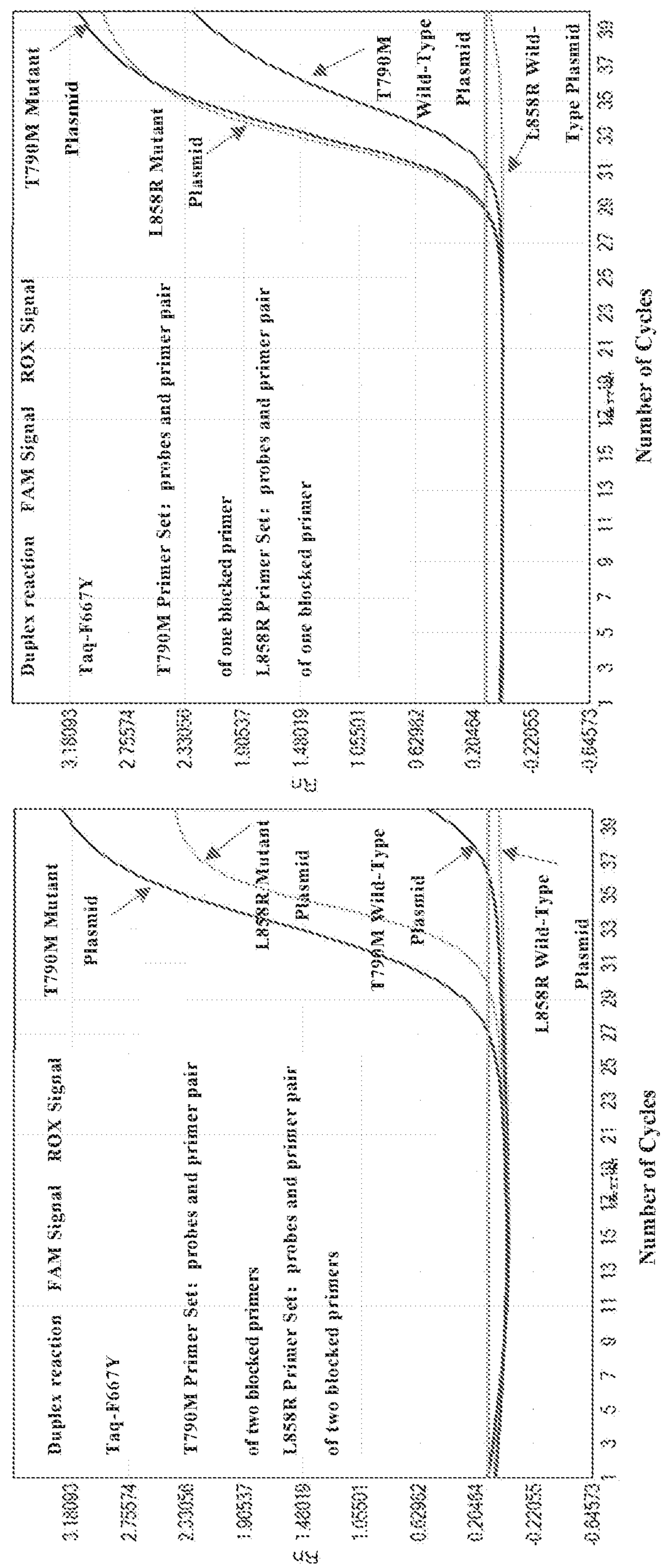
FIG. 3A shows the results of Taq-F667Y for multiplex amplification of mutant and wild-type plasmids by fluorescent PCR with a primer-activated polymerization combined with probes.

The fluorescent PCR reaction system used Taq-F667Y, an enzyme with pyrophosphatase activity, 5'→3' DNA polymerase activity and 5'→3' nucleic acid exonuclease activity at the same time. When 20,000 copies of T790M mutant plasmids and 20,000 copies of L858R mutant plasmids were used as mixed templates to amplify the corresponding mutant gene fragment with different primer pools aforementioned, respectively, a fluorescent amplification signal was generated; when 20,000 copies of T790M wild-type plasmid and 20,000 copies of L858R wild-type plasmid were used as mixed templates for amplification, it was found that the T790M primer sets (probes and primer pair of two blocked primers or probes and primer pair of one blocked primer) both showed a non-specific amplification signal, with the T790M primer set of probe and primer pair of one blocked primer performing worse, while the L858R primer sets (probes and primer pair of two blocked primers or probes and primer pair of one blocked primer) both showed no fluorescent amplification signal (Table 2, FIG. 3A). Regardless of singleplex or multiplex reactions, the fluorescent PCR method, which was based on the combination of primer-activated polymerization and probes, used Taq-F667Y and generated non-specific amplification for T790M (2369C>T) mutation detection under the condition of wild-type templates, but the primer set of probes and primer pair of two blocked primers shows better specificity than the primer set of probes and primer pair of one blocked primer.

Example 3.2 Mutation Detection with Taq-F667Y/CA

The primer sets used in Example 3.2 are the same as those used in Example 3.1.

Figure 3B:
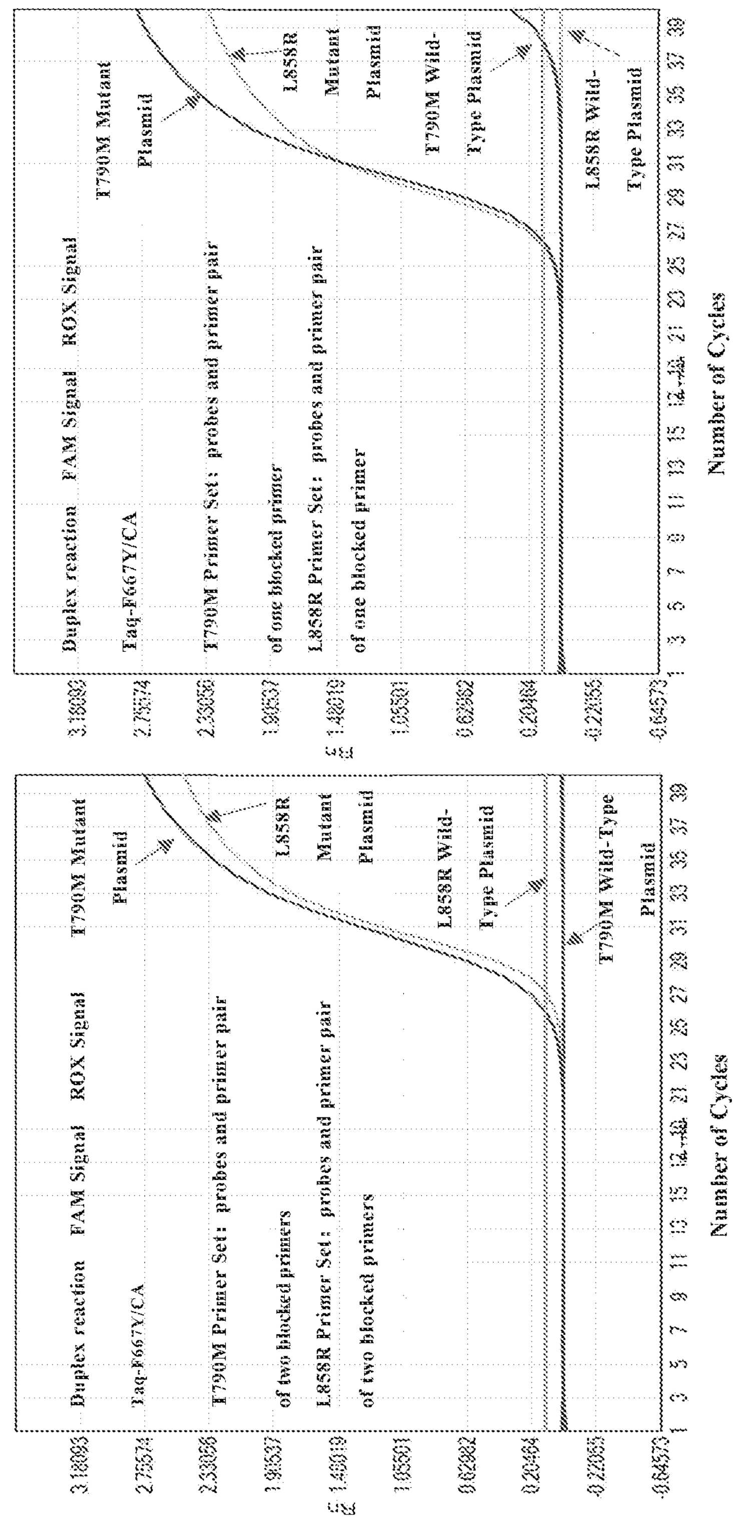
FIG. 3B shows the results of Taq-F667Y/CA for multiplex amplification of mutant and wild-type plasmids by fluorescent PCR with a primer-activated polymerization combined with probes.

The fluorescent PCR reaction system used Taq-F667Y, an enzyme with pyrophosphatase activity, 5'→3' DNA polymerase activity and 5'→3' nucleic acid exonuclease activity at the same time. When 20,000 copies of T790M mutant plasmids and 20,000 copies of L858R mutant plasmids were used as mixed templates to amplify the corresponding mutant gene fragment with different primer pools aforementioned, respectively, a fluorescent amplification signal was generated; when 20,000 copies of T790M wild-type plasmids and 20,000 copies of L858R wild-type plasmids were used as mixed templates for amplification, it was found that the T790M and L858R primer sets of probes and primer pair of two blocked primers both showed a non-specific amplification signal while the T790M primer pair (probes and primer pair of one blocked primer) had a weak non-specific amplification signal (Ct 38.19) (Table 2, FIG. 3B). Based on the combination of primer-activated polymerization and probes, the fluorescent PCR method used modified Taq DNA polymerase, such as citric anhydride-modified Taq-F667Y/CA to perform singleplex or multiplex detection, indicating higher amplification specificity than unmodified Taq-F667Y. Also, the primer set of probes and primer pair of two blocked primers shows better specificity than the primer set of probes and primer pair of one blocked primer.

Example 3.3 Mutation Detection with the Combination of KlenTaq-s and Taq/CA

The primer sets used in Example 3.3 are the same as those used in Example 3.1.

Figure 3C:
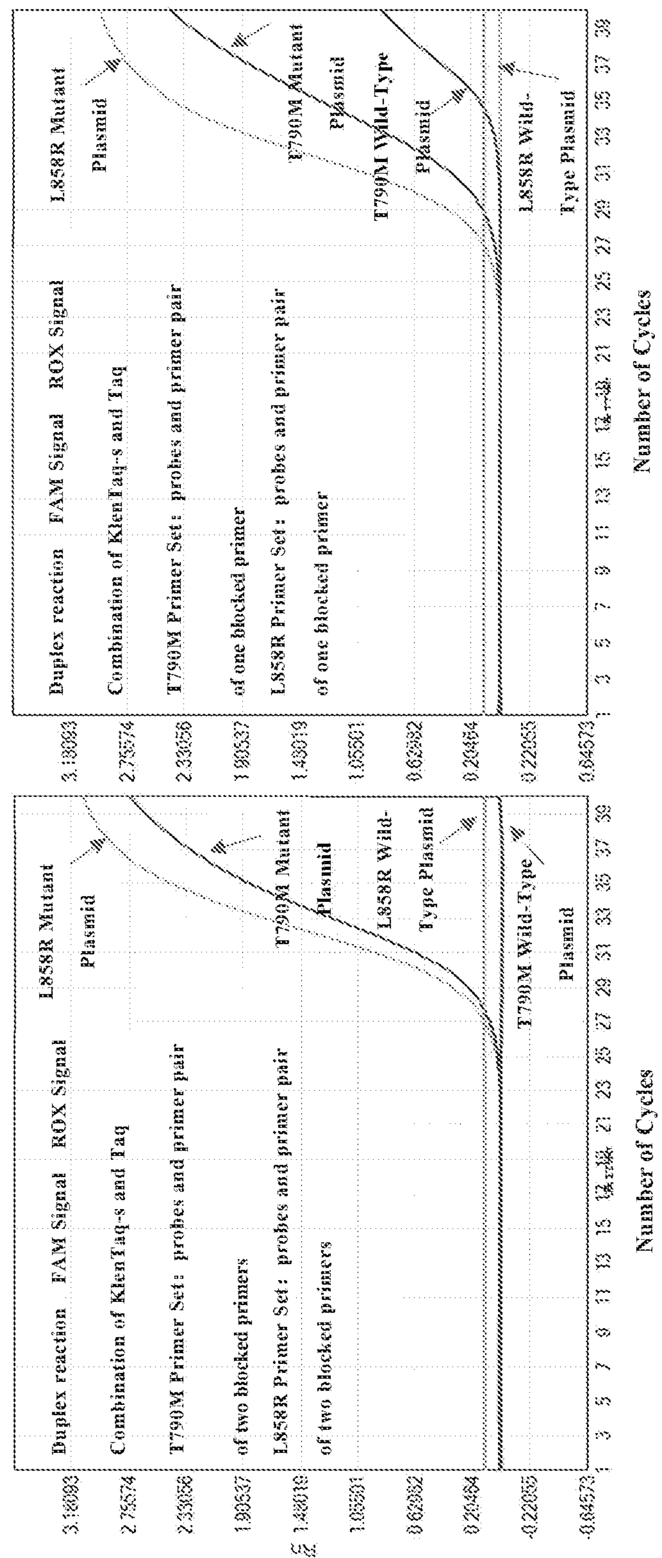
FIG. 3C shows the results of KlenTaq-s in combination with Taq/CA for multiplex amplification of mutant and wild-type plasmids by fluorescent PCR with a primer-activated polymerization combined with probes.

The fluorescent PCR reaction system used a combination of KlenTaq-s and Taq/CA, utilizing the pyrophosphatase activity and the 5'→3' DNA polymerase activity of KlenTaq-s, combined with the 5'→3' DNA polymerase activity and 5'→3' nucleic acid exonuclease activity of Taq enzyme activity. When 20,000 copies of T790M mutant plasmids and 20,000 copies of L858R mutant plasmids were used as mixed templates to amplify the corresponding mutant gene fragment with different primer pools aforementioned, respectively, a fluorescent amplification signal was generated; when 20,000 copies of T790M wild-type plasmids and 20,000 copies of L858R wild-type plasmids were used as mixed templates for amplification, it was found that the T790M and L858R primer sets of probes and primer pair of two blocked primers both showed a non-specific amplification signal while the T790M primer pair (probes and primer pair of one blocked primer) had a non-specific amplification signal (Table 2, FIG. 3C). Based on the combination of primer-activated polymerization and probes, the fluorescent PCR method used the combination of KlenTaq-s and Taq/CA for multiplex detection, which indicated a similar result as Taq-F667Y/CA that the primer set of probes and primer pair of two blocked primers shows better specificity than the primer set of probes and primer pair of one blocked primer. Based on the combination of primer-activated polymerization and probes, the fluorescent PCR method used the combination of KlenTaq-s and Taq/CA to perform singleplex and multiplex detection and had excellent specificity, indicating that the combination of KlenTaq-s and Taq/CA has comparable amplification specificity to Taq-F667Y/CA.

Comparing Taq-F667Y, Taq-F667Y/CA and the combined enzymes of KlenTaq-s and Taq/CA, Taq-F667Y/CA or the combination of KlenTaq-s and Taq/CA are preferable; comparing the primer set of probes and primer pair of two blocked primers with the primer set of probes and primer pair of one blocked primer, the primer set of probes and primer pair of two blocked primers is preferable.

TABLE 1

Primer combinations for EGFR gene mutation detection

| Gene Mutation Type | Base Mutation | Primer Sequence Number (SEQ ID NO) | Primer Sequence (5'-3') |
|---|---|---|---|
| T790M | 2369C>T | 1 | ACCTCCACCGTGCAGCTCATCA**ddT** |
| | | 2 | TTTGTGTTCCCGGACATAGTCC**ddA** |
| | | 3 | TTTGTGTTCCCGGACATAGTCC**A** |
| | | 4 | FAM-AGCCGAAGGGCATGAGCT-MGB |

TABLE 1-continued

| Primer combinations for EGFR gene mutation detection | | | |
|---|---|---|---|
| Gene Mutation Type | Base Mutation | Primer Sequence Number (SEQ ID NO) | Primer Sequence (5'-3') |
| L858R | 2573T>G | 5 | CAGCATGTCAAGATCACAGATTTTGGGC**ddG** |
| | | 6 | CCTCCTTACTTTGCCTCCTTCT**ddG** |
| | | 7 | CCTCCTTACTTTGCCTCCTTCT**G** |
| | | 8 | ROX-CTGGGTGCGGAAGAGAAAGAATACC-MGB |

TABLE 2

| Results of EGFR gene mutation detection by singleplex and duplex fluorescent PCR Assays | | | | | | | | | |
|---|---|---|---|---|---|---|---|---|---|
| Gene Mutation Type | Base Mutation | DNA Polymerase | Primer Sequence Number (SEQ ID NO) | 3' terminal blocked group | Fluorophore-quencher dual-labeling | Singleplex detection for mutant plasmids Ct | Singleplex detection for wild-type plasmids Ct[a] | Duplex detection for mutant plasmids Ct | Duplex detection for wild-type plasmids Ct[a] |
| T790M | 2369C > T | Taq-F667Y | 1 | ddTMP | None | 26.74 | 37.35 | 27.01 | 36.16 |
| | | | 2 | ddAMP | None | | | | |
| | | | 4 | None | FAM-MBG | | | | |
| L858R | 2573T > G | | 5 | ddGMP | None | 28.31 | 40.00 | 29.61 | 40.00 |
| | | | 6 | ddGMP | None | | | | |
| | | | 8 | None | ROX-MGB | | | | |
| T790M | 2369C > T | Taq-F667Y | 1 | ddTMP | None | 27.22 | 36.71 | 28.81 | 31.02 |
| | | | 3 | None | None | | | | |
| | | | 4 | None | FAM-MBG | | | | |
| L858R | 2573T > G | | 5 | ddGMP | None | 27.20 | 40.00 | 28.59 | 40.00 |
| | | | 7 | None | None | | | | |
| | | | 8 | None | ROX-MGB | | | | |
| T790M | 2369C > T | Taq-F667Y/CA | 1 | ddTMP | None | 26.02 | 40.00 | 26.00 | 40.00 |
| | | | 2 | ddAMP | None | | | | |
| | | | 4 | None | FAM-MBG | | | | |
| L858R | 2573T > G | | 5 | ddGMP | None | 26.87 | 40.00 | 27.10 | 40.00 |
| | | | 6 | ddGMP | None | | | | |
| | | | 8 | None | ROX-MGB | | | | |
| T790M | 2369C > T | Taq-F667Y/CA | 1 | ddTMP | None | 25.64 | 40.00 | 26.38 | 38.19 |
| | | | 3 | None | None | | | | |
| | | | 4 | None | FAM-MBG | | | | |
| L858R | 2573T > G | | 5 | ddGMP | None | 25.20 | 40.00 | 26.17 | 40.00 |
| | | | 7 | None | None | | | | |
| | | | 8 | None | ROX-MGB | | | | |
| T790M | 2369C > T | Enzyme combination of Klen | 1 | ddTMP | None | 26.30 | 40.00 | 27.67 | 40.00 |
| | | | 2 | ddAMP | None | | | | |
| | | | 4 | None | FAM-MBG | | | | |
| L858R | 2573T > G | Taq-s and Taq/CA | 5 | ddGMP | None | 25.75 | 40.00 | 27.06 | 40.00 |
| | | | 6 | ddGMP | None | | | | |
| | | | 8 | None | ROX-MGB | | | | |
| T790M | 2369C > T | Enzyme combination of Klen | 1 | ddTMP | None | 26.87 | 40.00 | 28.87 | 34.55 |
| | | | 3 | None | None | | | | |
| | | | 4 | None | FAM-MBG | | | | |
| L858R | 2573T > G | Taq-s and Taq/CA | 5 | ddGMP | None | 24.24 | 40.00 | 27.03 | 40.00 |
| | | | 7 | None | None | | | | |
| | | | 8 | None | ROX-MGB | | | | |

Notes of Table 2:

1. [a]means that the assay has no Ct value, and the Ct value is replaced by 40, indicating that the product of the amplification reaction is not detected.

All of the literature referred to in the present disclosure is cited by reference in the present application as if each literature was cited separately as a reference. It is further understood that after reading above teachings of the present disclosure, various changes or modifications may be made to the present disclosure by those skilled in the art, and that such equivalent forms likewise fall within the scope of the claims appended to the present application.

The invention claimed is:

1. A method for detecting nucleic acids by fluorescent PCR, comprising:

preparing a PCR reaction system, said PCR reaction system comprising:

(i) a nucleic acid sample comprising or suspected of comprising a target sequence;

(ii) a nucleic acid polymerase or a combination of nucleic acid polymerases, having a 5'→3' polymerase activity, a 5'→3' exonuclease activity, and a pyrophosphatase activity, wherein the nucleic acid polymerase or the combination of nucleic acid polymerases is (1) Taq DNA polymerase with the F667Y mutation which is modified with citraconic anhydride (Taq-F667Y/CA), or (2) Taq DNA polymerase with N fragment truncated and the F667Y mutation (KlenTaq-s) in combination with a Taq DNA polymerase modified with citraconic anhydride (Taq/CA);

(iii) a primer pair for amplifying said target sequence to produce an amplicon, said primer pair comprising at least one blocked primer which comprises a 2',3'-dideoxyribonucleotide located at the 3' end of the blocked primer, wherein said 2',3'-dideoxyribonucleotide blocks the extension of said nucleic acid polymerase or combination of nucleic acid polymerases when said 2',3'-dideoxyribonucleotide does not anneal to said target sequence or said amplicon, (iv) pyrophosphate, wherein in the presence of the pyrophosphate said nucleic acid polymerase or a combination of nucleic acid polymerases is capable of using the pyrophosphatase activity to remove said 2',3'-dideoxyribonucleotide from said blocked primer when said 2',3'-dideoxyribonucleotide anneals to said target sequence or said amplicon, allowing said nucleic acid polymerase or combination of nucleic acid polymerases to use the 5'→3' polymerase activity to extend from said blocked primer, wherein said nucleic acid polymerase or a combination of nucleic acid polymerases is unable to remove said 2',3'-dideoxyribonucleotide from said blocked primer when said 2',3'-dideoxyribonucleotide does not anneal to said target sequence or said amplicon; and (v) a fluorescent probe which is different from the blocked primer and complementary to the target sequence or the amplicon, wherein said fluorescent probe comprises a first nucleotide linked to a fluorophore and a second nucleotide linked to a quencher, wherein the fluorescence signal of said fluorophore is quenched by said quencher when said first nucleotide is not hydrolyzed from said fluorescent probe, and wherein said nucleic acid polymerase or combination of nucleic acid polymerases is capable of using the 5'→3' exonuclease activity to hydrolyze said first nucleotide from said fluorescent probe bound to said target sequence or said amplicon during extension from the blocked primer such that the fluorescence signal of said fluorophore is not quenched by said quencher;

subjecting said PCR reaction system to amplification reactions under appropriate reaction conditions; and detecting the fluorescence signal of said PCR reaction system.

2. The method of claim 1, wherein said target sequence comprises a mutant nucleotide, and wherein said 2',3'-dideoxyribonucleotide is complementary to said mutant nucleotide.

3. The method of claim 1, wherein said fluorophore of the fluorescent probe is selected from the group consisting of: FAM, VIC, JOE, NED, TET, HEX, TAMRA, ROX, TEXASRED, CY3, CY5, CY5.5, and CY7.

4. The method of claim 1, wherein said quencher of the fluorescent probe is selected from the group consisting of: BHQ1, BHQ2, BHQ3, Dabcyl, MGB, and TAMARA.

5. The method of claim 1, wherein said blocked primer further comprises a mismatched nucleotide which is not complimentary to said target sequence when said blocked primer anneals to said target sequence.

6. The method of claim 5, wherein said mismatched nucleotide and said fluorescent probe are complimentary to each other.

7. The method of claim 5, wherein said mismatched nucleotide is 2-18 nucleotides apart from said blocked nucleotide.

8. The method of claim 1, wherein said blocked primer has a length of 8 to 70 nucleotides.

9. The method of claim 1, wherein said nucleic acid sample comprises modified or unmodified single-stranded DNA, double-stranded DNA, RNA, cRNA or a combination thereof.

10. The method of claim 1, said PCR reaction system further comprising:

(vi) a second primer pair for amplifying a second target sequence to generate a second amplicon, said second primer pair comprising a second blocked primer which comprises a second 2',3'-dideoxyribonucleotide located at the 3' end of the second blocked primer, wherein said second 2',3'-dideoxyribonucleotide blocks the extension of said nucleic acid polymerase or combination of nucleic acid polymerases when said second 2',3'-dideoxyribonucleotide does not anneal to said second target sequence or said second amplicon, and (vii) a second fluorescent probe complementary to the second target sequence or the second amplicon, said second fluorescent probe comprising a third nucleotide linked to a second fluorophore and a fourth nucleotide linked to a second quencher, wherein the fluorescence signal of said second fluorophore is quenched by said second quencher when said third nucleotide is not hydrolyzed from said probe, and wherein said nucleic acid polymerase or combination of nucleic acid polymerases is capable of hydrolyzing said third nucleotide from said second fluorescent probe bound to said target sequence or amplicon during extension such that the fluorescence signal of said second fluorophore is not quenched by said second quencher.

11. A method for detecting nucleic acids by fluorescent PCR, comprising:

preparing a PCR reaction system, said PCR reaction system comprising:

(i) a nucleic acid sample comprising or suspected of comprising a target sequence;

(ii) a nucleic acid polymerase or a combination of nucleic acid polymerases, having a 5'→3' polymerase activity, a 5'→3' exonuclease activity, and a pyrophosphatase activity, wherein the nucleic acid polymerase or the combination of nucleic acid polymerases is (1) Taq-F667Y/CA, or (2) KlenTaq-s in combination with Taq/CA;

(iii) a plurality of primer pairs for separately amplifying said plurality of target sequences to produce a plurality of amplicons, wherein each primer pair comprises a respective blocked primer which comprises a 2',3'-dideoxyribonucleotide located at the 3' end of the blocked primer, wherein said 2',3'-dideoxyribonucleotide blocks the extension of said nucleic acid polymerase or combination of nucleic acid polymerases when said 2',3'-dideoxyribonucleotide does not anneal to said target sequence or said amplicon, (iv) pyrophosphate, wherein in the presence of the pyrophosphate said nucleic acid polymerase or a combination of nucleic acid polymerases is capable of using the pyrophosphatase activity to remove said 2',3'-dideoxyribonucleotide from the blocked primer when the 2',3'-dideoxyribonucleotide anneals to said target sequence or said amplicon, allowing said nucleic acid polymerase or combination of nucleic acid polymerases to use the 5'→3' polymerase activity to extend from the blocked primer, wherein said nucleic acid polymerase or a combination of nucleic acid polymerases is unable to remove said 2',3'-dideoxyribonucleotide from the blocked primer when the 2',3'-dideoxyribonucleotide does not anneal to said target sequence or said amplicon; and (v) a plurality of fluorescent probes which are different from the blocked primers and complementary to said plurality of target sequences or corresponding amplicon, respectively, wherein each fluorescent probe comprises a first nucleotide attached to a fluorophore and a second nucleotide attached to a quencher, respectively, wherein the fluorescence signal of said fluorophore is quenched by said quencher when said first nucleotide is not hydrolyzed from said fluorescent probe, and wherein said nucleic acid polymerase or combination of nucleic acid polymerases is capable of using the 5'→3' exonuclease activity to hydrolyze said first nucleotide from said fluorescent probe bound to the target sequence or amplicon during extension from the respective blocked primer, wherein said plurality of fluorescent probes comprises the same or different fluorophores;

subjecting said PCR reaction system to amplification reactions under appropriate reaction conditions; and detecting the fluorescence signal of said PCR reaction system.

* * * * *